(12) United States Patent
Puffer et al.

(10) Patent No.: US 12,091,716 B2
(45) Date of Patent: Sep. 17, 2024

(54) METHODS AND MATERIALS FOR IDENTIFYING AND TREATING TRAUMATIC BRAIN INJURY

(71) Applicant: Mayo Foundation for Medical Education and Research, Rochester, MN (US)

(72) Inventors: Ross C. Puffer, Rochester, MN (US); Ian F. Parney, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 684 days.

(21) Appl. No.: 17/150,926

(22) Filed: Jan. 15, 2021

(65) Prior Publication Data

US 2021/0214796 A1 Jul. 15, 2021

Related U.S. Application Data

(60) Provisional application No. 62/961,343, filed on Jan. 15, 2020.

(51) Int. Cl.
*C12N 15/11* (2006.01)
*C12Q 1/6883* (2018.01)

(52) U.S. Cl.
CPC ...... *C12Q 1/6883* (2013.01); *C12Q 2600/112* (2013.01); *C12Q 2600/178* (2013.01)

(58) Field of Classification Search
CPC .................... C12Q 2600/112; C12Q 2600/178
See application file for complete search history.

(56) References Cited

U.S. PATENT DOCUMENTS 8,211,653 B2  7/2012 Klass et al.

FOREIGN PATENT DOCUMENTS

| ES | 2419129 | 8/2013 |
|---|---|---|
| WO | WO 2017019976 | 2/2017 |
| WO | WO 2018175941 | 9/2018 |

OTHER PUBLICATIONS

Stiver , Complications of decompressive craniectomy for traumatic brain injury, Neurosurg Focus, 2009, 26 (6):E7, pp. 1-16 (Year: 2009).*
Atif et al., "A Review of MicroRNA Biomarkers in Traumatic Brain Injury," J. Exp. Neuroscience, Mar. 8, 2019, 13:1-12.
Bhomia et al., "A Panel of Serum MiRNA Biomarkers for the Diagnosis of Severe to Mild Traumatic Brain Injury in Humans," Sci. Reports, Jun. 24, 2016, 6:28148, 12 pages.
Chang et al., "Roles of microRNA-1 in hypoxia-induced apoptotic insults to neuronal cells," Arch. Toxicology, Sep. 20, 2014, 90(1):191-202.
Chen et al., "MicroRNA Expression Profiles Identify Biomarker for Differentiating the Embolic Stroke from Thrombotic Stroke," Biomed. Res. International, Dec. 6, 2018, 2018:4514178, 6 pages.
Cheng et al., "Exploring the potential value of miR-148b-3p, miR-151b and miR-27b-3p as biomarkers in acute ischemic stroke," Biosci. Reports, Nov. 28, 2018, 38(6):BSR20181033, 8 pages.
Cumba Garcia et al., "Isolation and analysis of plasma-derived exosomes in patients with glioblastoma," J. Immunology, May 2018, 200(1S):178.37, 4 pages.
Cumba Garcia et al., "Isolation and Analysis of Plasma-Derived Exosomes in Patients With Glioma," Front. Oncology, Jul. 16, 2019, 9:651, 9 pages.
Di Pietro, "MicroRNAs as Novel Biomarkers for the Diagnosis and Prognosis of Mild and Severe Traumatic Brain Injury," J. Neurotrauma, Jun. 1, 2017, 34(11):1948-1956.
He et al., "Zhenbao pill protects against acute spinal cord injury via miR-146a-5p regulating the expression of GPR17," Biosci. Reports, Jan. 19, 2018, 38(1):BSR20171132, 12 pages.
Heijnen et al., "Activated Platelets Release Two Types of Membrane Vesicles: Microvesicles by Surface Shedding and Exosomes Derived From Exocytosis of Multivesicular Bodies and a-Granules," Blood, Dec. 1, 1999, 94(11):3791-3799.
Hinzman et al., "Plasma-derived extracellular vesicles yield predictive markers of cranial irradiation exposure in mice," Sci. Reports, Jul. 1, 2019, 9:9460, 9 pages.
Karnati et al., "Neuronal Enriched Extracellular Vesicle Proteins as Biomarkers for Traumatic Brain Injury," J. Neurotrauma, Apr. 1, 2019, 36(7):975-987.
Karttunen et al., "Extracellular Vesicles as Diagnostics and Therapeutics for Structural Epilepsies," Int. J. Mol Sciences, Mar. 13, 2019, 20(6):1259, 22 pages.
Ko et al., "Diagnosis of traumatic brain injury using miRNA signatures in nanomagnetically isolated brain-derived extracellular vesicles," Lab Chip, Dec. 7, 2018, 18(23):3617-3630.
Ko et al., "Multi-Dimensional Mapping of Brain-Derived Extracellular Vesicle MicroRNA Biomarker for Traumatic Brain Injury Diagnostics," J. Neurotrauma, May 6, 2019, 37(22):2424-2434.
Korley et al., "Emergency Department Evaluation of Traumatic Brain Injury in the United States, 2009-2010," J. Head Trauma Rehabilitation, Nov. 2016, 31(6):379-387.
Korley et al., "Performance Evaluation of a Multiplex Assay for Simultaneous Detection of Four Clinically Relevant Traumatic Brain Injury Biomarkers," J. Neurotrauma, Jul. 23, 2018, 36(1):182-187.
Kowal et al., "Biogenesis and secretion of exosomes," Curr. Opin. Cell Biology, Aug. 2014, 29:116-125.
LaRocca et al., "Comparison of serum and saliva miRNAs for identification and characterization of mTBI in adult mixed martial arts fighters," PLoS One, Jan. 2, 2019, 14(1):e0207785, 38 pages.
Li et al., "Glioma microvesicles carry selectively packaged coding and non-coding RNAs which alter gene expression in recipient cells," RNA Biology, Aug. 2013, 10(8):1333-1344.

(Continued)

*Primary Examiner* — Ekaterina Poliakova-Georgantas
(74) *Attorney, Agent, or Firm* — Fish & Richardson P.C.

(57) ABSTRACT

This document provides methods and materials involved in identifying mammals as having, or being likely to have, a traumatic brain injury (TBI). This document also provides methods for treating mammals identified as having, or being likely to have, a TBI, based on the identification methods described herein.

8 Claims, 7 Drawing Sheets

Specification includes a Sequence Listing.

(56) References Cited

OTHER PUBLICATIONS

Li et al., "MiR-27a ameliorates inflammatory damage to the blood-spinal cord barrier after spinal cord ischemia: reperfusion injury in rats by downregulating TICAM-2 of the TLR4 signaling pathway," J. Neuroinflammation, Feb. 2015, 12:25, 13 pages.

Manek et al., "Protein Biomarkers and Neuroproteomics Characterization of Microvesicles/Exosomes from Human Cerebrospinal Fluid Following Traumatic Brain Injury," Mol. Neurobiology, Nov. 29, 2017, 55(7):6112-6128.

Mathivanan et al., "Proteomics Analysis of A33 Immunoaffinity-purified Exosomes Released from the Human Colon Tumor Cell Line LIM1215 Reveals a Tissue-specific Protein Signature," Mol. Cell Proteomics, Feb. 2010, 9(2):197-208.

McMahon et al., "Symptomatology and functional outcome in mild traumatic brain injury: results from the prospective TRACK-TBI study," J. Neurotrauma, Jan. 2014, 31(1):26-33.

Okonkwo et al., "GFAP-BDP as an acute diagnostic marker in traumatic brain injury: results from the prospective transforming research and clinical knowledge in traumatic brain injury study," J. Neurotrauma, Sep. 2013, 30(17):1490-1497.

Pitt et al., "Extracellular vesicles: masters of intercellular communication and potential clinical interventions," J. Clin. Investigation, Apr. 1, 2016, 126(4):1139-1143.

Proia et al., "Astrocytes shed extracellular vesicles that contain fibroblast growth factor-2 and vascular endothelial growth factor," Int. J. Mol. Medicine, Jan. 2008, 21(1):63-67.

Puffer et al., "Plasma extracellular vesicles as a source of biomarkers in traumatic brain injury," J. Neurosurgery, Jul. 24, 2020, 134(6):1921-1928.

Sabirzhanov, "Downregulation of miR-23a and miR-27a following Experimental Traumatic Brain Injury Induces Neuronal Cell Death through Activation of Proapoptotic Bcl-2 Proteins," J. Neuroscience, Jul. 23, 2014, 34(30):10055-10071.

Schiera et al., "Neurons produce FGF2 and VEGF and secrete them at least in part by shedding extracellular vesicles," J. Cell. Mol. Medicine, Nov. 2007, 11(6):1384-1394.

Seabury et al., "Assessment of Follow-up Care After Emergency Department Presentation for Mild Traumatic Brain Injury and Concussion: Results From the TRACK-TBI Study," JAMA Netw. Open, May 25, 2018, 1(1):e180210, 13 pages.

Sharma et al., "Identification of Serum MicroRNA Signatures for Diagnosis of Mild Traumatic Brain Injury in a Closed Head Injury Model," PLoS One, Nov. 7, 2014, 9(11):e112019, 20 pages.

Tigchelaar, "MicroRNA biomarkers for acute traumatic spinal cord injury," Thesis for the degree of Doctor of Philosophy, The University of British Columbia, May 2019, 221 pages.

Yang et al., "Applications of cerebrospinal miRNA in the detection and treatment of acute CNS injury," Front. Lab. Medicine, Jun. 2018, 2(2):83-88.

Zeng et al., "Inhibition of miR-143 during ischemia cerebral injury protects neurones through recovery of the hexokinase 2-mediated glucose uptake," Biosci. Reports, Jul. 4, 2017, 37(4):BSR20170216, 9 pages.

Zhang et al., "MiR-214-3p attenuates cognition defects via the inhibition of autophagy in SAMP8 mouse model of sporadic Alzheimer's disease," Neurotoxicology, Sep. 2016, 56:139-149.

\* cited by examiner

METHODS AND MATERIALS FOR IDENTIFYING AND TREATING TRAUMATIC BRAIN INJURY

CROSS-REFERENCE TO RELATED APPLICATIONS

This application claims the benefit of U.S. Provisional Application Ser. No. 62/961,343, Jan. 15, 2020. The disclosure of the prior application is considered part of (and is incorporated by reference in) the disclosure of this application.

TECHNICAL FIELD

This document relates to methods and materials for identifying and treating traumatic brain injury.

BACKGROUND

Traumatic brain injury (TBI) is a leading cause of death in men under 35, and is increasingly recognized as a contributor to chronic neurological dysfunction. Plasma biomarkers such as glial fibrillary acidic protein (GFAP) in TBI have been identified.

SUMMARY

This document is based, at least in part, on the identification of extracellular vesicles (EVs) and their contents as biomarkers of TBI. EVs are nanoscale membrane-encapsulated particles released by cells. Plasma EVs have been utilized as a source of biomarkers for cancer, but have not been extensively evaluated in other pathologies. As described herein, EVs can be isolated from peripheral blood after TBI, and brain-specific biomarkers contained therein can be analyzed and used for diagnosis, assessing prognosis, and monitoring treatment of TBI patients. The methods provided herein can be particularly useful, in some cases, in the emergency department for detecting evidence of TBI in cases where a computed tomography (CT) scan may be negative. Given that patients can develop post-TBI brain dysfunction even with a negative CT scan, identifying these cases may be important to guide diagnosis and/or treatment. These methods may also be relevant to diagnosing a concussion in the early phase of injury, as well as tracking recovery in the following days/weeks.

This document provides methods and materials involved in identifying mammals with TBI (e.g., humans with TBI). For example, this document provides methods and materials for detecting the presence of EVs containing an altered level of one or more microRNAs (miRNAs) (e.g., hsa-miR-1-3p, hsa-miR-143-3p, hsa-miR-151b, hsa-miR-27a-3p, hsa-miR-29a-3p, hsa-miR-328-3p, hsa-miR-9-3p, hsa-miR-99a-5p, hsa-miR-99b-5p, hsa-miR-155-5p, and/or hsa-miR-30c-5p) in a biological sample (e.g., an EV-containing blood or serum sample) from a mammal, thereby identifying the mammal as being more likely to have a TBI than a mammal that does not exhibit an altered level of the one or more miRNAs or other markers. Conversely, this document provides methods and materials for determining that a biological sample from a mammal does not have an altered level of the one or more miRNAs or other markers, thereby identifying the mammal as being less likely to have a TBI than a mammal that does exhibit an altered level of the one or more miRNAs or other markers. Identifying mammals as having or not having an altered level of one or more of the markers listed herein can allow clinicians to proceed with proper clinical surveillance (e.g., frequency of clinical follow-ups and/or need for surveillance biopsies) and treatment options for potential TBI patients.

This document also provides methods and materials involved in treating mammals identified as having a TBI. These markers can provide valuable information with regard to ongoing brain injury after an initial TBI, and can guide treatment decisions such as blood pressure management, cerebrospinal fluid (CSF) diversion, or even invasive surgical decompression. In the post-treatment phase, the markers can assist with tracking the effectiveness of these or other directed treatments. For example, this document provides methods and materials for administering blood pressure management, CSF diversion, or invasive surgical decompression, based at least in part on the markers described herein. In addition, mammals identified as being likely to have a severe TBI can undergo more regular surveillance (e.g., examination on a more frequent basis) to assess symptoms or effects of the TBI.

In a first aspect, this document features a method for identifying a mammal as having a TBI or as being likely to have a TBI. The method can include identifying a mammal as having EVs with an altered level of one or more miRNAs as compared to the level of the one or more miRNAs in EVs from a corresponding mammal that does not have a TBI, where the one or more miRNAs are selected from the group consisting of hsa-miR-1-3p (SEQ ID NO:2), hsa-miR-143-3p (SEQ ID NO:3), hsa-miR-151b (SEQ ID NO:4), hsa-miR-27a-3p (SEQ ID NO:5), hsa-miR-29a-3p (SEQ ID NO:6), hsa-miR-328-3p (SEQ ID NO:7), hsa-miR-9-3p (SEQ ID NO:8), hsa-miR-99a-5p (SEQ ID NO:9), hsa-miR-99b-5p (SEQ ID NO:10), hsa-miR-155-5p (SEQ ID NO:11), and hsa-miR-30c-5p (SEQ ID NO:12). The mammal can be a human. The EVs can be from a blood sample obtained from the mammal. The blood sample can be a plasma sample. The method can include identifying the mammal as having EVs with altered levels of two or more of the miRNAs, as compared to levels of the two or more miRNAs in EVs from a corresponding mammal that does not have a TBI. The method can include identifying the mammal as having EVs with an increased level of one or more miRNAs selected from the group consisting of hsa-miR-1-3p (SEQ ID NO:2), hsa-miR-143-3p (SEQ ID NO:3), hsa-miR-151b (SEQ ID NO:4), hsa-miR-27a-3p (SEQ ID NO:5), hsa-miR-29a-3p (SEQ ID NO:6), hsa-miR-328-3p (SEQ ID NO:7), hsa-miR-9-3p (SEQ ID NO:8), hsa-miR-99a-5p (SEQ ID NO:9), and hsa-miR-99b-5p (SEQ ID NO:10), as compared to a corresponding mammal that does not have a TBI. The method can include identifying the mammal as having EVs with a decreased level of one or more miRNAs selected from the group consisting of hsa-miR-155-5p (SEQ ID NO:11) and hsa-miR-30c-5p (SEQ ID NO:12), as compared to a corresponding mammal that does not have a TBI. The method can include identifying the mammal as having EVs with an increased level of one or more miRNAs selected from the group consisting of hsa-miR-1-3p (SEQ ID NO:2), hsa-miR-143-3p (SEQ ID NO:3), hsa-miR-151b (SEQ ID NO:4), hsa-miR-27a-3p (SEQ ID NO:5), hsa-miR-29a-3p (SEQ ID NO:6), hsa-miR-328-3p (SEQ ID NO:7), hsa-miR-9-3p (SEQ ID NO:8), hsa-miR-99a-5p (SEQ ID NO:9), and hsa-miR-99b-5p (SEQ ID NO:10), and as having a decreased level of one or more miRNAs selected from the group consisting of hsa-miR-155-5p (SEQ ID NO:11) and hsa-miR-30c-5p (SEQ ID NO:12), as compared to a corresponding mammal that does not have a TBI.

In another aspect, this document features a method that includes (a) identifying a mammal as having EVs with an altered level of one or more miRNAs as compared to a level of the one or more miRNAs in EVs from a corresponding mammal that does not have a TBI, where the miRNAs are selected from the group consisting of hsa-miR-1-3p (SEQ ID NO:2), hsa-miR-143-3p (SEQ ID NO:3), hsa-miR-151b (SEQ ID NO:4), hsa-miR-27a-3p (SEQ ID NO:5), hsa-miR-29a-3p (SEQ ID NO:6), hsa-miR-328-3p (SEQ ID NO:7), hsa-miR-9-3p (SEQ ID NO:8), hsa-miR-99a-5p (SEQ ID NO:9), hsa-miR-99b-5p (SEQ ID NO:10), hsa-miR-155-5p (SEQ ID NO:11), and hsa-miR-30c-5p (SEQ ID NO:12), thereby identifying the mammal as having or being likely to have a TBI, and (b) treating the mammal by one or more of (i) administering a medication to manage blood pressure, cerebral perfusion pressure, or intracranial pressure, (ii) administering an antibiotic, (iii) surgically removing a mass or lesion from the brain, and (iv) decompressing the brain via direct craniectomy and bone removal, where the treating reduces the effects of a TBI in the mammal. The mammal can be a human. The EVs can be from a blood sample obtained from the mammal. The blood sample can be a plasma sample. The method can include identifying the mammal as having EVs with altered levels of two or more of the miRNAs, as compared to levels of the two or more miRNAs in EVs from a corresponding mammal that does not have a TBI. The method can include identifying the mammal as having EVs with an increased level of one or more miRNAs selected from the group consisting of hsa-miR-1-3p (SEQ ID NO:2), hsa-miR-143-3p (SEQ ID NO:3), hsa-miR-151b (SEQ ID NO:4), hsa-miR-27a-3p (SEQ ID NO:5), hsa-miR-29a-3p (SEQ ID NO:6), hsa-miR-328-3p (SEQ ID NO:7), hsa-miR-9-3p (SEQ ID NO:8), hsa-miR-99a-5p (SEQ ID NO:9), and hsa-miR-99b-5p (SEQ ID NO:10), as compared to a corresponding mammal that does not have a TBI. The method can include identifying the mammal as having EVs with a decreased level of one or more miRNAs selected from the group consisting of hsa-miR-155-5p (SEQ ID NO:11) and hsa-miR-30c-5p (SEQ ID NO: 12), as compared to a corresponding mammal that does not have a TBI. The method can include identifying the mammal as having EVs with an increased level of one or more miRNAs selected from the group consisting of hsa-miR-1-3p (SEQ ID NO:2), hsa-miR-143-3p (SEQ ID NO:3), hsa-miR-151b (SEQ ID NO:4), hsa-miR-27a-3p (SEQ ID NO:5), hsa-miR-29a-3p (SEQ ID NO:6), hsa-miR-328-3p (SEQ ID NO:7), hsa-miR-9-3p (SEQ ID NO:8), hsa-miR-99a-5p (SEQ ID NO:9), and hsa-miR-99b-5p (SEQ ID NO:10), and as having a decreased level of one or more miRNAs selected from the group consisting of hsa-miR-155-5p (SEQ ID NO:11) and hsa-miR-30c-5p (SEQ ID NO:12), as compared to a corresponding mammal that does not have a TBI.

In another aspect, this document features a method for treating a mammal having a TBI, where the mammal was identified as having EVs with an altered level of one or more miRNAs as compared to a level of the one or more miRNAs in EVs from a corresponding mammal that does not have a TBI, where the one or more miRNAs are selected from the group consisting of hsa-miR-1-3p (SEQ ID NO:2), hsa-miR-143-3p (SEQ ID NO:3), hsa-miR-151b (SEQ ID NO:4), hsa-miR-27a-3p (SEQ ID NO:5), hsa-miR-29a-3p (SEQ ID NO:6), hsa-miR-328-3p (SEQ ID NO:7), hsa-miR-9-3p (SEQ ID NO:8), hsa-miR-99a-5p (SEQ ID NO:9), hsa-miR-99b-5p (SEQ ID NO:10), hsa-miR-155-5p (SEQ ID NO: 11), and hsa-miR-30c-5p (SEQ ID NO:12), and where the method includes treating the mammal by one or more of (a) administering a medication to manage blood pressure, cerebral perfusion pressure, or intracranial pressure, (b) administering an antibiotic, (c) surgically removing a mass or lesion from the brain, and (d) decompressing the brain via direct craniectomy and bone removal, where the treating reduces the effects of TBI in the mammal. The mammal can be a human. The EVs can be from a blood sample obtained from the mammal. The blood sample can be a plasma sample. The mammal can be identified as having EVs with altered levels of two or more of the miRNAs, as compared to the levels of the two or more miRNAs in EVs from a corresponding mammal that does not have a TBI. The mammal can be identified as having EVs with an increased level of one or more miRNAs selected from the group consisting of hsa-miR-1-3p (SEQ ID NO:2), hsa-miR-143-3p (SEQ ID NO:3), hsa-miR-151b (SEQ ID NO:4), hsa-miR-27a-3p (SEQ ID NO:5), hsa-miR-29a-3p (SEQ ID NO:6), hsa-miR-328-3p (SEQ ID NO:7), hsa-miR-9-3p (SEQ ID NO:8), hsa-miR-99a-5p (SEQ ID NO:9), and hsa-miR-99b-5p (SEQ ID NO:10), as compared to a corresponding mammal that does not have a TBI. The mammal can be identified as having EVs with a decreased level of one or more miRNAs selected from the group consisting of hsa-miR-155-5p (SEQ ID NO:11) and hsa-miR-30c-5p (SEQ ID NO:12), as compared to a corresponding mammal that does not have a TBI. The mammal can be identified as having EVs with an increased level of one or more miRNAs selected from the group consisting of hsa-miR-1-3p (SEQ ID NO:2), hsa-miR-143-3p (SEQ ID NO:3), hsa-miR-151b (SEQ ID NO:4), hsa-miR-27a-3p (SEQ ID NO:5), hsa-miR-29a-3p (SEQ ID NO:6), hsa-miR-328-3p (SEQ ID NO:7), hsa-miR-9-3p (SEQ ID NO:8), hsa-miR-99a-5p (SEQ ID NO:9), and hsa-miR-99b-5p (SEQ ID NO:10), and as having a decreased level of one or more miRNAs selected from the group consisting of hsa-miR-155-5p (SEQ ID NO:11) and hsa-miR-30c-5p (SEQ ID NO:12), as compared to a corresponding mammal that does not have a TBI.

In another aspect, this document features a method for clearing a mammal for normal activity, wherein the mammal had a TBI or is suspected of having a TBI. The method comprises (or consists essentially or consists of) (a) identifying the mammal as having EVs that comprise levels of hsa-miR-1-3p (SEQ ID NO:2), hsa-miR-143-3p (SEQ ID NO:3), hsa-miR-151b (SEQ ID NO:4), hsa-miR-27a-3p (SEQ ID NO:5), hsa-miR-29a-3p (SEQ ID NO:6), hsa-miR-328-3p (SEQ ID NO:7), hsa-miR-9-3p (SEQ ID NO:8), hsa-miR-99a-5p (SEQ ID NO:9), hsa-miR-99b-5p (SEQ ID NO:10), hsa-miR-155-5p (SEQ ID NO:11), and hsa-miR-30c-5p (SEQ ID NO:12) that are less than 5 percent altered as compared to the levels of the miRNAs in EVs from a corresponding mammal that does not have a TBI, and (b) instructing the mammal to resume one or more normal activities. The mammal can be a human. The EVs can be from a blood sample obtained from the mammal. The blood sample can be a plasma sample. The method can comprise instructing the mammal to resume a sporting activity.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF DRAWINGS

FIGS. 1A-1E provide results from nanoparticle tracking analyses. This figure includes representative histograms (FIGS. 1A and 1B) and photomicrographs (FIGS. 1C and 1D) of EV analysis in a healthy control (FIGS. 1A and 1C) and a TBI patient (FIGS. 1B and 1D). The histograms in both the healthy control (FIG. 1A) and TBI patient (FIG. 1B) demonstrate a substantial exosome peak (<100 nm) and multiple smaller microvesicle peaks (>100 nm).

FIGS. 3A and 3B show plasma exosomal RNA levels. In particular.

DETAILED DESCRIPTION

Severe TBI affects more than 200,000 individuals annually in the United States and is a leading cause of mortality in men under 35 years (Korley et al., *J Head Trauma Rehabil* 2016, 31:379-387). The symptoms/effects of TBI can range from mild to severe, and may include loss of consciousness, mild to severe headache, nausea or vomiting, dilation of pupils, loss of coordination, sleeping disorders, convulsion, dizziness or fatigue, loss of balance, sensory symptoms, blurred vision, double vision, ringing sound in ears, loss of ability to smell, sensitivity to light or sound, mental symptoms, memory problems, alexia, speaking disorder, dysgraphia, mood swings, depression or anxiety, and/or coma. Mild TBI is under-reported, but may be as much as ten times more common than severe TBI, and is increasingly recognized as a contributor to chronic neurological dysfunction (McMahon et al., *J Neurotrauma* 2014, 31:26-33; and Seabury et al., *JAMA Netw Open* 2018, 1:e180210). Plasma biomarkers in TBI have generated excitement, with identification of multiple brain-specific molecules (e.g., GFAP, UCH-L1, NF-1, and tau) in the blood of TBI patients, and with FDA approval of a device (Brain Trauma Indicator) for rapid measurement of GFAP and UCH-L1 levels in plasma (Korley et al., *J Neurotrauma* 2018, 36(1) doi: 10.1089/neu.2017.5623). These biomarkers can be used to help clarify TBI diagnosis and prognosis, particularly in mild TBI.

EVs are membrane-bound particles released by the majority of human cells, including cells within the central nervous system (Heijnen et al., *Blood* 1999, 94:3791-3799; and Kowal et al., *Curr Opin Cell Biol* 2014, 29:116-125). EVs contain DNA, messenger RNA (mRNA), non-coding RNA, and proteins that are released into the microenvironment, and play key roles in cell-to-cell communication between neurons, glia and endothelial cells for complex functions including moderation of the blood-brain barrier (Li et al., *RNA Biol* 2013, 10:1333-1344; Proia et al., *Int J Mol Med* 2008, 21:63-67; and Schiera et al., *J Cell Mol Med* 2007, 11:1384-1394). EVs are a heterogeneous group that includes microvesicles (>100 nm) and smaller exosomes (<100 nm) that are generated through distinct cellular pathways and have distinct cargo. EVs have generated significant interest in neuro-oncology, as tumor-derived EVs shape the microenvironment by down-regulating the immune response and upregulating angiogenic factors, among other complex actions (Li et al., supra; Prioa et al., supra; Schiera et al., supra; and Mathivanan et al., *Mol Cell Proteomics* 2010, 9:197-208).

EVs have not been extensively studied in TBI, although one study identified a higher number of EVs in cerebrospinal fluid (CSF) of two subjects with severe (GCS 3-8) TBI compared to normal controls, and further isolated both GFAP and UCHL-1 in higher quantities in the TBI subjects compared to controls (Manek et al., *Mol Neurobiol* 2018, 55:6112-6128).

EVs in peripheral blood provide a lipid-membrane bound container of DNA, RNA, and proteins that are protected from circulating degradation enzymes, and therefore may provide a snapshot of the microenvironment in specific organ systems shortly before the peripheral blood sample is taken. In the studies described herein, plasma samples from TBI patients and healthy controls were used to assess plasma EVs as a biomarker source in TBI. These studies demonstrated the feasibility of isolating EVs, characterized EV size and frequency, and revealed the presence of both established (GFAP) and novel (short non-coding RNA) TBI biomarkers within EVs.

This document provides methods and materials for identifying and/or treating patients who have, or who are at an increased likelihood of having, a TBI, or mammals having, or being at an increased likelihood of having, a severe TBI as compared to a mild TBI. For example, this document provides methods and materials for identifying a mammal (e.g., a human) as having a TBI (e.g., a severe TBI or a mild TBI). Any appropriate mammal can be identified as having a TBI as described herein. For example, humans and other primates such as monkeys having can be identified as having a TBI as described herein. In some cases, dogs, cats, horses, cows, pigs, sheep, mice, or rats can be identified as having a TBI as described herein.

As described herein, a mammal (e.g., a human) can be identified as having (or as being likely to have) a TBI by detecting the presence of EVs with altered levels of one or more markers. Examples of markers that can be evaluated and used to classify a mammal (e.g., a human) as having or not having a TBI (e.g., a severe TBI) include, without limitation, miRNAs such as hsa-miR-1-3p (SEQ ID NO:2), hsa-miR-143-3p (SEQ ID NO:3), hsa-miR-151b (SEQ ID NO:4), hsa-miR-27a-3p (SEQ ID NO:5), hsa-miR-29a-3p (SEQ ID NO:6), hsa-miR-328-3p (SEQ ID NO:7), hsa-miR- 9-3p (SEQ ID NO:8), hsa-miR-99a-5p (SEQ ID NO:9), hsa-miR-99b-5p (SEQ ID NO:10), hsa-miR-155-5p (SEQ ID NO:11), and hsa-miR-30c-5p (SEQ ID NO:12).

In some embodiments, an miRNA marker provided herein can have a nucleotide sequence that is at least 90% (e.g., at least 91%, 92%, 93%, 94%, 95%, 96%, 97%, 98%, or 99%) identical to a sequence as set forth in any of SEQ ID NOs:2-12. The percent sequence identity between a particular nucleic acid or amino acid sequence and a sequence referenced by a particular sequence identification number is determined as follows. First, a nucleic acid or amino acid sequence is compared to the sequence set forth in a particular sequence identification number using the BLAST 2 Sequences (Bl2seq) program from the stand-alone version of BLASTZ containing BLASTN version 2.0.14 and BLASTP version 2.0.14. This stand-alone version of BLASTZ can be obtained online at fr.com/blast or at ncbi.nlm.nih.gov. Instructions explaining how to use the Bl2seq program can be found in the readme file accompanying BLASTZ. Bl2seq performs a comparison between two sequences using either the BLASTN or BLASTP algorithm. BLASTN is used to compare nucleic acid sequences, while BLASTP is used to compare amino acid sequences. To compare two nucleic acid sequences, the options are set as follows: -i is set to a file containing the first nucleic acid sequence to be compared (e.g., C:\seq1.txt); -j is set to a file containing the second nucleic acid sequence to be compared (e.g., C:\seq2.txt); -p is set to blastn; -o is set to any desired file name (e.g., C:\output.txt); -q is set to -l; -r is set to 2; and all other options are left at their default setting. For example, the following command can be used to generate an output file containing a comparison between two sequences: C:\Bl2seq -i c:\seq1.txt -j c:\seq2.txt -p blastn -o c:\output.txt -q -l -r 2. To compare two amino acid sequences, the options of Bl2seq are set as follows: -i is set to a file containing the first amino acid sequence to be compared (e.g., C:\seq1.txt); -j is set to a file containing the second amino acid sequence to be compared (e.g., C:\seq2.txt); -p is set to blastp; -o is set to any desired file name (e.g., C:\output.txt); and all other options are left at their default setting. For example, the following command can be used to generate an output file containing a comparison between two amino acid sequences: C:\Bl2seq -i c:\seq1.txt -j c:\seq2.txt -p blastp -o c:\output.txt. If the two compared sequences share homology, then the designated output file will present those regions of homology as aligned sequences. If the two compared sequences do not share homology, then the designated output file will not present aligned sequences.

Once aligned, the number of matches is determined by counting the number of positions where an identical nucleotide residue is presented in both sequences. The percent sequence identity is determined by dividing the number of matches either by the length of the sequence set forth in the identified sequence or by an articulated length (e.g., 100 consecutive bases from a sequence set forth in an identified sequence), followed by multiplying the resulting value by 100. For example, the reference human miRNA sequence set forth in SEQ ID NO:2 is 22 nucleotides in length. A nucleotide sequence that has 21 matches when aligned with the reference sequence is 95.5 percent identical to the reference sequence (i.e., 21/22×100=95.5). It is noted that the percent sequence identity value is rounded to the nearest tenth. For example, 75.11, 75.12, 75.13, and 75.14 are rounded down to 75.1, while 75.15, 75.16, 7.17, 75.18, and 7.19 are rounded up to 7.2. It also is noted that the length value will always be an integer.

EVs can be obtained from any appropriate biological sample (e.g., blood, plasma, serum, or cerebrospinal fluid) using any appropriate method (e.g., density gradient ultracentrifugation or microfluidics). Any appropriate method can be used to determine if a mammal (e.g., a human) has altered (e.g., elevated or reduced) levels of one or more of the miRNA markers described herein. The term "elevated level" or "increased level" as used herein with respect to a miRNA level refers to a level of miRNA present within or otherwise associated with EVs that is greater (e.g., at least 5, 10, 25, 35, 45, 50, 55, 65, 75, 80, 90, or 100 or more percent greater) than the median level of that miRNA within or otherwise associated with control EVs from a mammal that does not have a TBI. The term "reduced level" or "decreased level" as used herein with respect to miRNA level refers to a level of miRNA present within or otherwise associated with EVs that is less (e.g., at least 5, 10, 25, 35, 45, 50, 55, 65, 75, 80, 90, or 100 percent less) than the median level of that miRNA within or otherwise associated with control EVs from a mammal that does not have a TBI. Appropriate methods for identifying EVs as having an elevated or reduced level of one or more miRNA markers as described herein include, without limitation, RNA sequencing and subsequent expression profiling, DNA sequencing and profiling, and protein characterization and profiling.

Once a mammal (e.g., a human) is identified as having EVs with altered (e.g., elevated or reduced) levels of one or more of the miRNAs described herein, the mammal can be classified as having, or being likely to have, a TBI. For example, a human identified as having EVs with altered levels of one or more (e.g., two, three, four, five, six, seven, eight, nine, ten, or all eleven) miRNAs selected from hsa-miR-1-3p (SEQ ID NO:2), hsa-miR-143-3p (SEQ ID NO:3), hsa-miR-151b (SEQ ID NO:4), hsa-miR-27a-3p (SEQ ID NO:5), hsa-miR-29a-3p (SEQ ID NO:6), hsa-miR-328-3p (SEQ ID NO:7), hsa-miR-9-3p (SEQ ID NO:8), hsa-miR-99a-5p (SEQ ID NO:9), hsa-miR-99b-5p (SEQ ID NO:10), hsa-miR-155-5p (SEQ ID NO:11), and hsa-miR-30c-5p (SEQ ID NO:12) can be classified as having, or being likely to have, a TBI. In some cases, a mammal (e.g., a human) identified as having EVs that do not exhibit altered levels of one or more (e.g., two, three, four, five, six, seven, eight, nine, ten, or all eleven) miRNAs selected from hsa-miR-1-3p (SEQ ID NO:2), hsa-miR-143-3p (SEQ ID NO:3), hsa-miR-151b (SEQ ID NO:4), hsa-miR-27a-3p (SEQ ID NO:5), hsa-miR-29a-3p (SEQ ID NO:6), hsa-miR-328-3p (SEQ ID NO:7), hsa-miR-9-3p (SEQ ID NO:8), hsa-miR-99a-5p (SEQ ID NO:9), hsa-miR-99b-5p (SEQ ID NO:10), hsa-miR-155-5p (SEQ ID NO:11), and hsa-miR-30c-5p (SEQ ID NO: 12) can be classified as not having, or not being likely to have, a TBI.

Any combination of markers can be evaluated. When increased levels of two miRNA markers are used to identify a mammal as having a TBI, for example, the two miRNAs can be hsa-mir-1-3p and hsa-mir-143-3p, hsa-mir-1-3p and hsa-mir-151b, hsa-mir-1-3p and hsa-mir-27a-3p, hsa-mir-1-3p and hsa-mir-29a-3p, hsa-mir-1-3p and hsa-mir-328-3p, hsa-mir-1-3p and hsa-mir-9-3p, hsa-mir-1-3p and hsa-mir-99a-5p, hsa-mir-1-3p and hsa-mir-99b-5p, hsa-mir-1-3p and hsa-mir-155-5p, hsa-mir-1-3p and hsa-mir-30c-5p, hsa-mir-143-3p and hsa-mir-151b, hsa-mir-143-3p and hsa-mir-27a-3p, hsa-mir-143-3p and hsa-mir-29a-3p, hsa-mir-143-3p and hsa-mir-328-3p, hsa-mir-143-3p and hsa-mir-9-3p, hsa-mir-143-3p and hsa-mir-99a-5p, hsa-mir-143-3p and hsa-mir-99b-5p, hsa-mir-143-3p and hsa-mir-155-5p, hsa-mir-143-3p and hsa-mir-30c-5p, hsa-mir-151b and hsa-mir-27a-3p, hsa-mir-151b and hsa-mir-29a-3p, hsa-mir-151b, and hsamir-328-3p, hsa-mir-151b and hsa-mir-9-3p, hsa-mir-151b and hsa-mir-99a-5p, hsa-mir-151b and hsa-mir-99b-5p, hsa-mir-151b and hsa-mir-155-5p, hsa-mir-151b and hsa-mir-30c-5p, hsa-mir-27a-3p and hsa-mir-29a-3p, hsa-mir-27a-3p and hsa-mir-328-3p, hsa-mir-27a-3p and hsa-mir-9-3p, hsa-mir-27a-3p and hsa-mir-99a-5p, hsa-mir-27a-3p and hsa-mir-99b-5p, hsa-mir-27a-3p and hsa-mir-155-5p, hsa-mir-27a-3p and hsa-mir-30c-5p, hsa-mir-29a-3p and hsa-mir-328-3p, hsa-mir-29a-3p and hsa-mir-9-3p, hsa-mir-29a-3p and hsa-mir-99a-5p, hsa-mir-29a-3p and hsa-mir-99b-5p, hsa-mir-29a-3p and hsa-mir-155-5p, hsa-mir-29a-3p and hsa-mir-30c-5p, hsa-mir-328-3p and hsa-mir-9-3p, hsa-mir-328-3p and hsa-mir-99a-5p, hsa-mir-328-3p and hsa-mir-99b-5p, hsa-mir-328-3p and hsa-mir-155-5p, hsa-mir-328-3p and hsa-mir-30c-5p, hsa-mir-9-3p and hsa-mir-99a-5p, hsa-mir-9-3p and hsa-mir-99b-5p, hsa-mir-9-3p and hsa-mir-155-5p, hsa-mir-9-3p and hsa-mir-30c-5p, hsa-mir-99a-5p and hsa-mir-99b-5p, hsa-mir-99a-5p and hsa-mir-155-5p, hsa-mir-99a-5p and hsa-mir-30c-5p, hsa-mir-99b-5p and hsa-mir-155-5p, hsa-mir-99b-5p and hsa-mir-30c-5p, or hsa-mir-155-5p and hsa-mir-30c-5p. Similarly, any combination of three, four, five, six, seven, eight, nine, ten, or all eleven of the aforementioned markers can be evaluated to determine whether a mammal has, or is likely to have, a TBI (e.g., a severe TBI).

As described herein, this document also provides methods and materials for treating a mammal identified as having, or as being likely to have, a TBI. Any appropriate mammal identified as having, or as being likely to have, a TBI can be treated by medical management such as, without limitation, administering one or more medications targeted to managing blood pressure, one or more medications targeted to managing cerebral perfusion pressure (e.g., vasopressors or antihypertensives), one or more medications targeted to managing intracranial pressure (e.g., mannitol or hypertonic saline), other medical interventions (e.g., one or more antibiotics to treat secondary infections), surgical treatment for removal of a mass or lesion or for decompression of the brain via direct craniectomy and bone removal, or any combination thereof. Having the ability to identify mammals who have or are likely to have a TBI can allow clinicians and patients to proceed with treatment options that mitigate the risk of longer term effects that can affect mammals with TBI. In addition, mammals identified as having, or being likely to have, a TBI can undergo more regular surveillance via, for example, examination and/or imaging studies (e.g., CT scans, MR images, or ultrasound-based techniques such as trans cranial Doppler studies) or invasive monitoring techniques through the use of an intracranial pressure monitor, a brain tissue oxygenation monitor, and/or an external ventricular drain, to detect changes in brain function early in its course.

The invention will be further described in the following example, which does not limit the scope of the invention described in the claims.

EXAMPLES

Example 1—Plasma Extracellular Vesicles as a Source of Biomarkers in TBI

Materials and Methods

Subjects: Subject plasma samples (about 500 µL each) were selected from the TRACK-TBI biorepository from the University of Pittsburgh (Okonkwo et al., *J Neurotrauma* 2013, 30:1490-1497). A total of 20 plasma samples were obtained, including 15 samples taken after TBI and 5 samples taken from healthy controls. Subjects with complicated mild (GCS 13-15 with evidence of injury on CT scan), moderate (GCS 9-12), and severe (GCS 3-8) TBI were included. Attempts were made to select subjects with a wide range of injury mechanisms accompanying all severities of TBI, as well as from uninjured, healthy controls. Demographic and injury information are listed in TABLE 1.

Isolation of EVs, western blot, and GFAP analysis: EVs within plasma were isolated using serial density gradient ultracentrifugation per a protocol described elsewhere (Cumba Garcia et al., *Frontiers Oncol* 2019, doi.org/10.3389/fonc.2019.00651). Concentrated EVs were then analyzed via nanotracker particle analysis using NanoSight (Malvern, NanoSight NS300). NanoSight allows for characterization of EVs, including both size and concentration, within a given sample. For western blot analysis, proteins were separated by electrophoresis on 4-20% SDS-PAGE. Following membrane transfer, the proteins were probed using the following antibodies: anti-Alix (Cell Signaling, #2171S, mouse monoclonal), anti-CD9 (Cell Signaling, #13174S, rabbit monoclonal), anti-CD63 (Santa Cruz Biotechnology, #sc-5275, mouse monoclonal) and anti-HSP90 (Cell Signaling, #4874S, rabbit polyclonal). The secondary antibody was horseradish peroxidase-conjugated goat anti-rabbit or goat anti-mouse (Jackson ImmunoResearch, #115-035-003, 111-035-003). Detection was by enhanced chemiluminescence (Thermo Fisher Scientific, #32106). For GFAP analysis, EVs were sonicated to break their membranes. GFAP expression was then tested in all samples via ELISA using a commercially available GFAP kit (abcam, cat #ab223867; Cambridge, MA) per the manufacturer's instructions.

Micro RNA analysis: Short non-coding RNA was isolated from samples using the miRNAeasy kit and QiaCube (Qiagen, Hilden, Germany). Preliminary quality assessment was performed using Nanodrop (Thermo-Fisher, Waltham, MA). Samples then underwent next generation sequencing using the Illumina MiSeq 2000 with NebNext multiplex oligos for Illumina adapters (the adapter sequence was AGATCGGAAGAGCACACGTCT; SEQ ID NO:1). Analysis of short non-coding RNA sequencing was performed in collaboration with the Bioinformatics Core of the Mayo Clinic Center for Individualized Medicine. Sequencing data were analyzed using the OASIS-2.0 platform with the reference genome HG38. This investigated 28,263 unique RNA entities covering miRNA, piRNA, snoRNA, snRNA, and rRNA species. Differential expression analysis was used to identify differences in miRNA expression between groups.

Statistical Analysis: Descriptive statistics with medians, interquartile range, and proportions were used to describe continuous and categorical variables, respectively. Biomarker levels were treated as continuous data. The Mann-Whitney U test was used to assess for between-group differences for continuous variables. All statistical analysis was performed with JMP software (JMP Cary, NC).

Results

Extracellular vesicles were isolated from 15 TBI subjects, including six CT-positive, mild TBI (GCS 13-15), three CT-positive, moderate TBI (GCS 9-12), and six CT-positive, severe TBI (GCS 3-8), as well as five healthy control subjects with no history of TBI or neurodegeneration. Given the relatively small sample size, subjects were divided into those who presented with an altered level of consciousness (GCS≤14) and those with a normal level of consciousness (GCS=15 and healthy controls) Demographic and injury information are listed in TABLE 1.

Figure 1A:
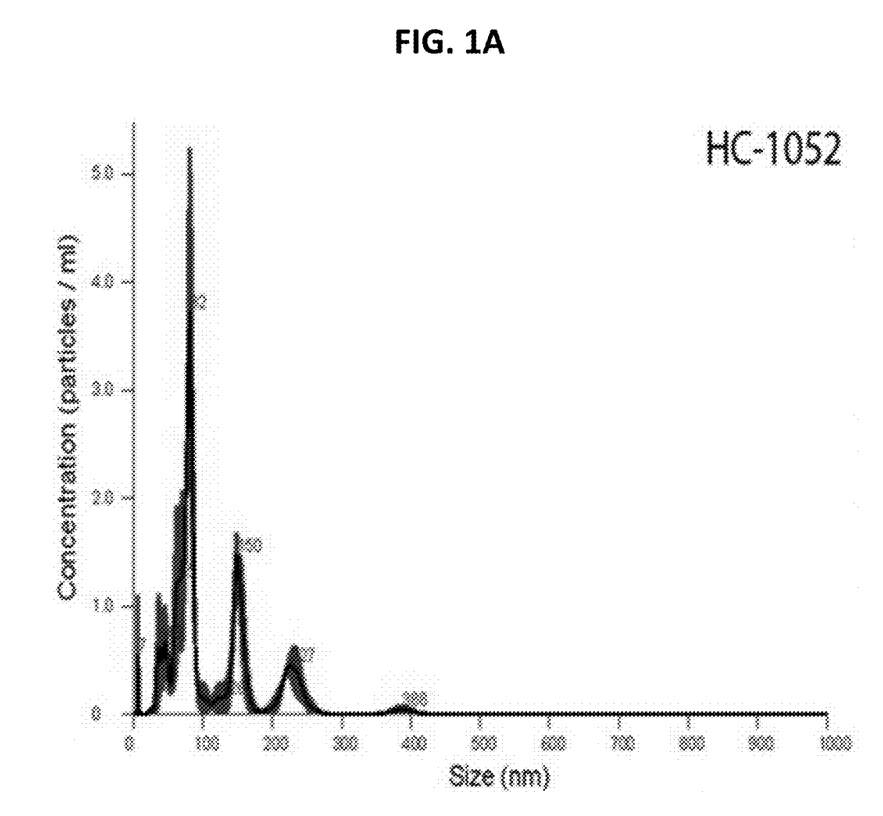
Figure 1B:
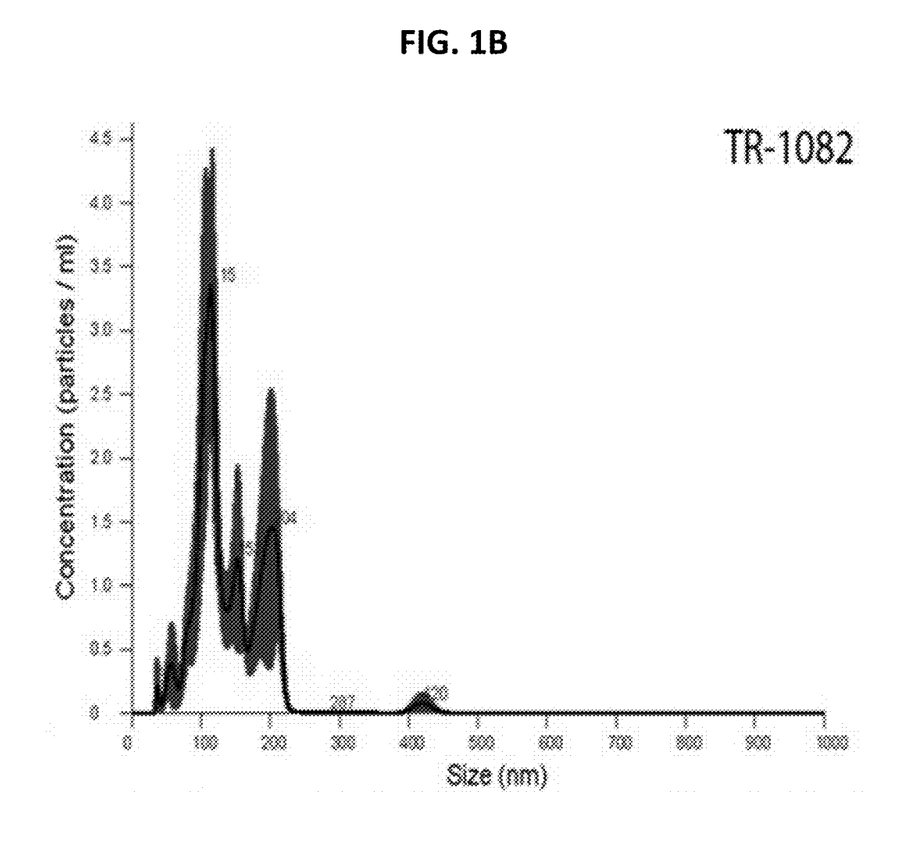
Figure 1C:
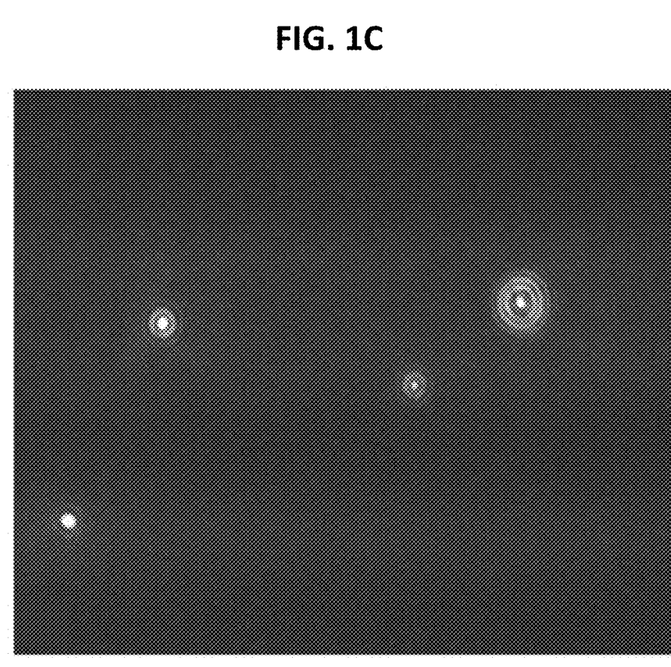
Figure 1D:
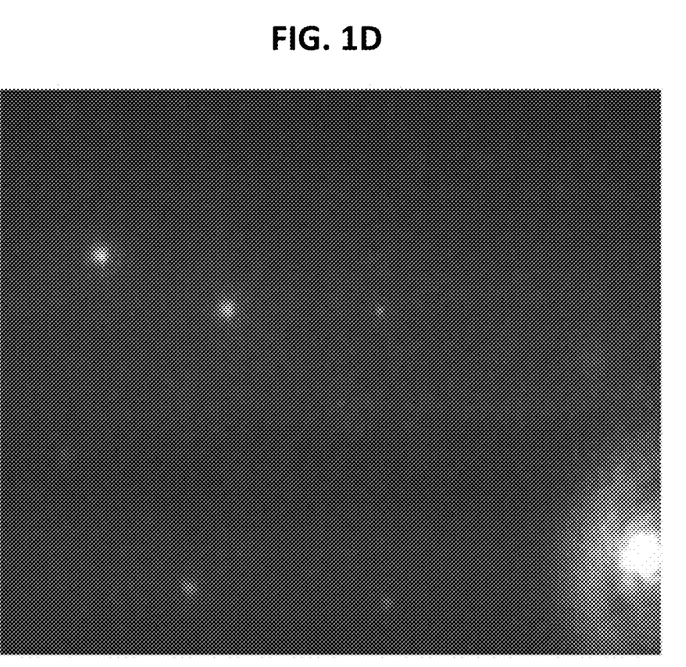
Figure 1E:
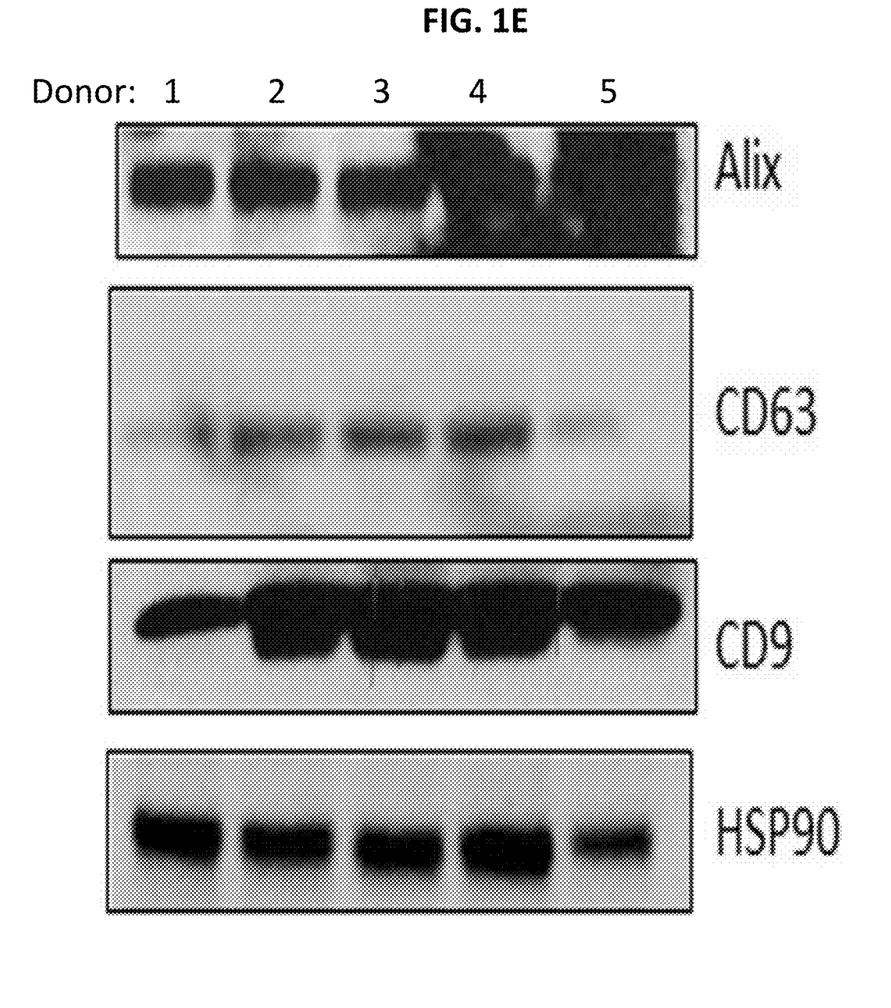
FIG. 1E is a western blot showing expression of common EV-associated proteins in EVs isolated from five donors with this protocol.
Figure 2A:
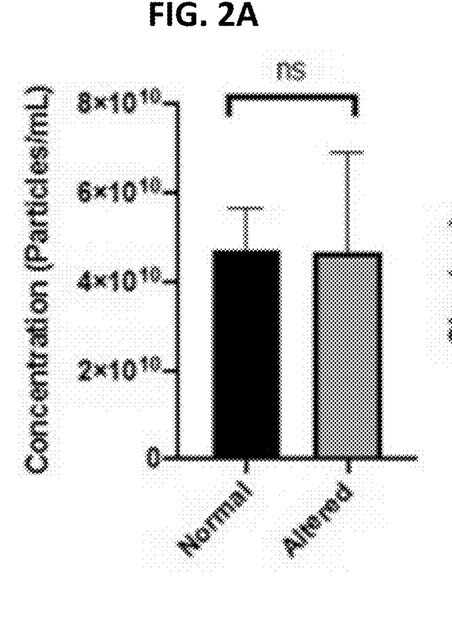
FIGS. 2A-2D show EV characteristics, with a comparison between TBI patients and normal donors with normal consciousness (Glasgow Coma Scale (GCS)=15) vs. TBI patients with altered consciousness (GCS<14) for EV concentration (FIG. 2A), EV size (FIG. 2B), EV GFAP yield (FIG. 2C), and EV RNA yield (FIG. 2D). It was notable that the GFAP yield was significantly higher in TBI patients with altered consciousness, but no significant differences were seen in EV concentration, size, or RNA yield. Values represent mean±standard error. $*p<0.05$.
Figure 2B:
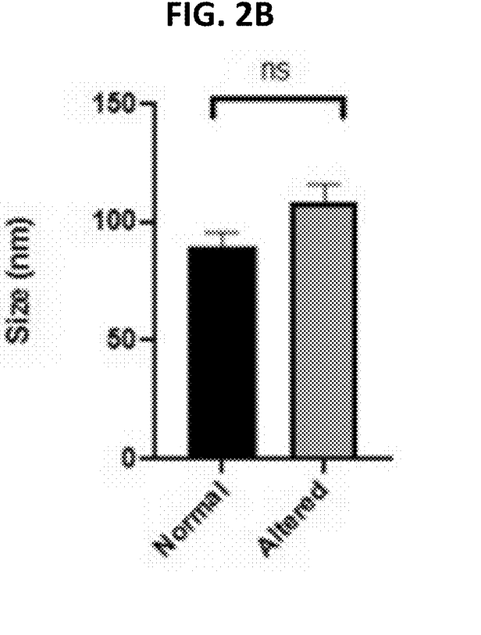
Figure 2C:
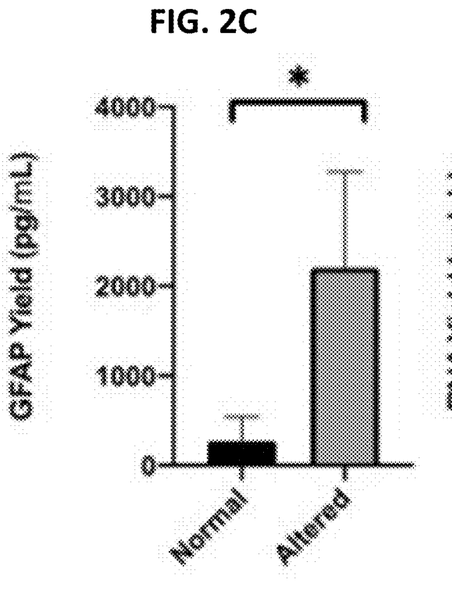
Figure 2D:
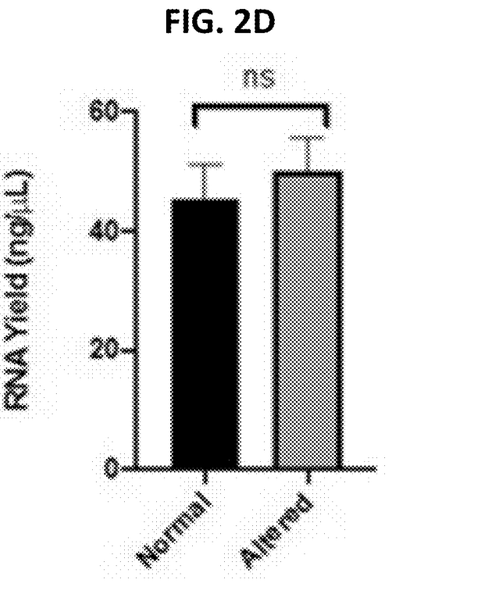

Isolation of EV's and GFAP analysis: EVs were successfully isolated in all samples analyzed. EV size and concentration were available for each sample. Data for a representative healthy control and a representative TBI subject are provided in the histograms of FIGS. 1A and 1B, respectively, and in the photomicrographs of FIGS. 1C and 1D, respectively. The histograms for both the healthy control (FIG. 1A) and the TBI patient (FIG. 1B) showed a substantial exosome peak (<100 nm) and multiple smaller microvesicle peaks (>100 nm). Common EV-associated proteins were assessed by Western blotting (FIG. 1E). EV size, concentration, GFAP concentration, and RNA yield for the entire cohort are shown in TABLE 2. There were no significant differences in EV size, concentration, or RNA yield between normal controls/TBI patients with normal consciousness (GCS=15) and TBI patients with altered consciousness (GCS≤14) (FIGS. 2A, 2B, and 2D). In contrast, analysis of GFAP yield by ELISA demonstrated significantly higher GFAP concentration in subjects with altered level of consciousness (GCS≤14) as compared to those with normal GCS (mean±standard error, GFAP concentration 2204.2 pg/mL+1067.2 pg/mL vs. 207.8 pg/mL+270.8 pg/mL, p=0.05; FIG. 2C).

Figure 3A:
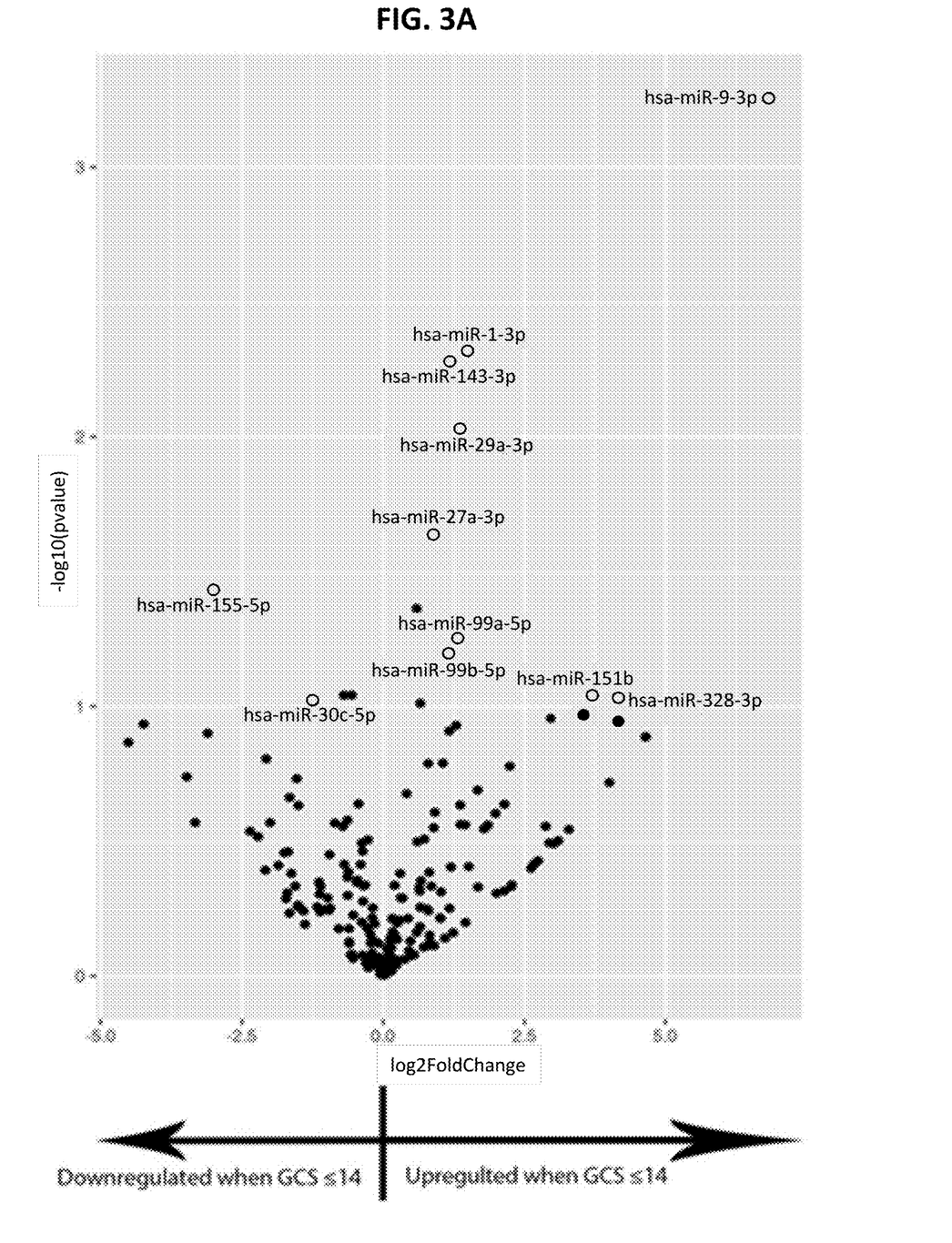
FIG. 3A is a volcano plot of differential microRNA expression, showing the fold change vs. p-value for microRNA sequences identified by short non-coding RNA sequencing of plasma EVs in TBI patients with altered consciousness (GCS≤14) vs. TBI patients and healthy controls with normal consciousness (GCS=15). Sequences trending to high differential expression (log 2 Fold Change >0.07 and p<0.1) are shown in open circles.
Figure 3B:
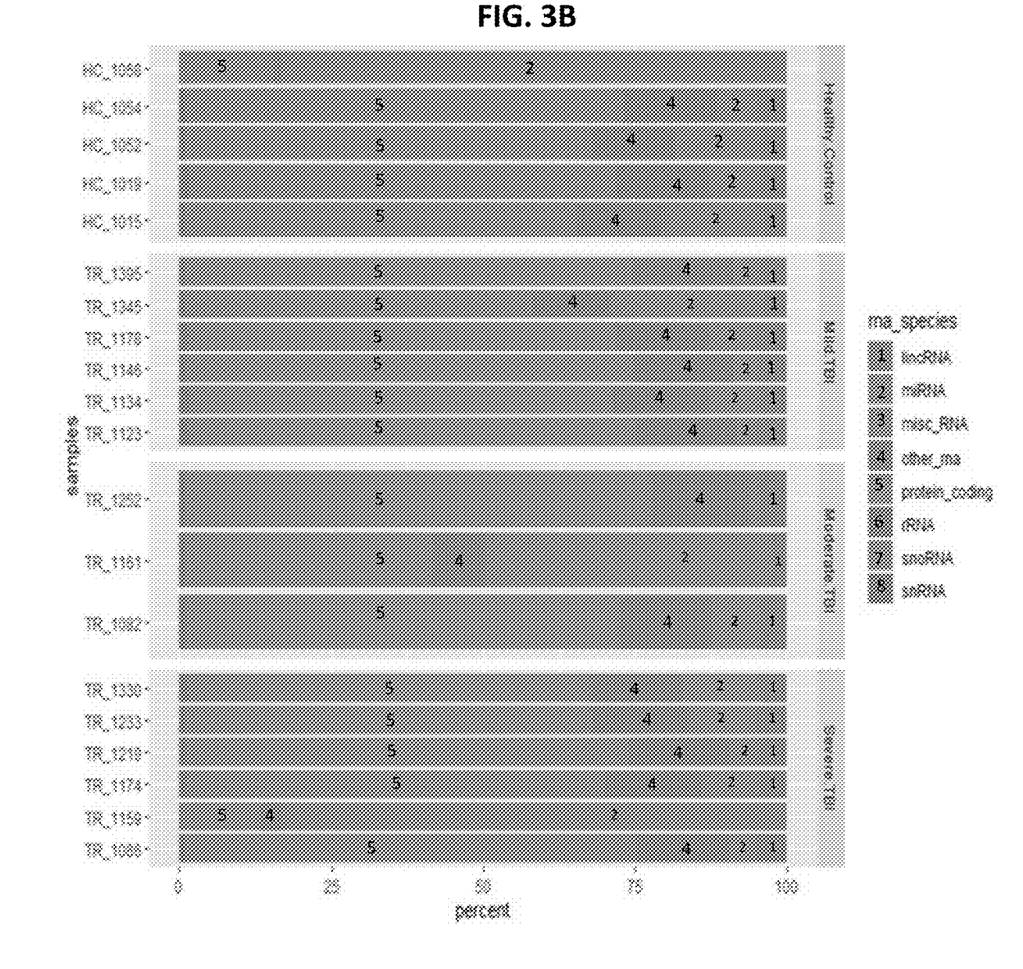
FIG. 3B is a graph plotting the relative frequency of miRNA vs. other RNA species in plasma exosomal RNA.

Short Non-Coding RNA Sequencing: RNA was successfully isolated from all samples, and RNA yields from the isolated EVs are listed in TABLE 2. Short non-coding RNA sequencing for plasma EVs from TBI patients and healthy controls were analyzed on the Illumina HiSeq 2500 platform and processed via a CAP-miRSeq pipeline. This allowed for unbiased identification of known and novel short non-coding RNA species beyond simply miRNAs. Differential expression analysis was performed for micro RNA sequences identified with thresholds of log 2 fold change [0.7] and a p-value <0.1 given the low number of samples with widely varying demographics, injury mechanism, and presentation GCS. Using these criteria, trends for nine highly upregulated miRNAs and two highly downregulated miRNAs were identified in TBI patients with an altered level of consciousness as compared to TBI patients and healthy controls with a normal level of consciousness (FIG. 3A, TABLES 3A and 3B). These reached statistical significance (p≤0.05) for 7 of the 11 individual miRNA sequences identified. Further, Ingenuity pathway analysis of highly differentially expressed miRNAs among all TBI patients relative to controls identified top disease and disorder pathways targeted, including cancer, gastrointestinal disease, and organismal injuries/abnormalities, while the top molecular and cellular pathways that were identified included cell death/survival, cell-to-cell signaling, and cellular assembly/organization (TABLE 4).

microRNAs have been well characterized in existing data-bases, which facilitated their analysis for the present study. However, microRNAs actually made up a minority of RNA species found within plasma EVs (FIG. 3B). The majority of the RNA found was actually protein-coding mRNA. Due to the specific parameters of the sequencing paradigm, which was aimed at short non-coding RNA, the protein-coding transcripts found in the present studies were not meaningfully quantified. Nevertheless, they were present in abundance. Similarly, multiple additional species of non-coding RNA were found, including small nucleolar RNA (snoRNA), small nuclear RNA (snRNA), ribosomal RNA (rRNA), and long intergenic noncoding RNA (lincRNA).

Thus, the studies described herein demonstrated that EVs can be isolated from peripheral blood after TBI, and indicated that they contain brain-specific biomarkers that can be analyzed and may be useful in the diagnosis, prognosis, and treatment monitoring of TBI.

TABLE 1

Cohort selected demographics, injury mechanism and presentation GCS

| TBI | Age | Sex | Injury Mechanism | Presentation GCS |
|---|---|---|---|---|
| TR-1345 | 22 | Female | MVC | 15 |
| TR-1134 | 41 | Male | MVC | 15 |
| TR-1146 | 32 | Male | Fall | 15 |
| TR-1395 | 46 | Male | MVC | 14 |
| TR-1178 | 25 | Male | MVC | 14 |
| TR-1123 | 72 | Male | Fall | 13 |
| TR-1161 | 33 | Male | Assault | 11 |
| TR-1252 | 24 | Male | MVC | 10 |
| TR-1082 | 55 | Female | Fall | 9 |
| TR-1330 | 35 | Male | Other | 6T |
| TR-1174 | 59 | Male | MVC | 3 |
| TR-1086 | 56 | Female | Fall | 3 |
| TR-1219 | 45 | Male | MVC | 3 |
| TR-1233 | 30 | Male | MVC | 3 |
| TR-1159 | 23 | Male | MVC | 3 |
| Healthy Control | | | | |
| HC-1054 | 25 | Male | N/A | 15 |
| HC-1052 | 31 | Male | N/A | 15 |
| HC-1015 | 40 | Male | N/A | 15 |
| HC-1019 | 53 | Female | N/A | 15 |
| HC-1058 | 63 | Male | N/A | 15 |

MVC = Motor Vehicle Collision

TABLE 2

MV/E concentration, mean size, GFAP concentration and RNA concentration

| | [MV/E] (particles/mL) | MV/E Size (nm) | [GFAP] (pg/mL) | [RNA] (ng/uL) |
|---|---|---|---|---|
| TBI | | | | |
| TR-1345 (GCS 15) | 36,300,000,000 | 85.2 | 2166.68 | 61.4 |
| TR-1134 (GCS 15) | 93,900,000,000 | 68.6 | Undetectable | 37.1 |
| TR-1146 (GCS 15) | 145,000,000,000 | 89.5 | Undetectable | 30.7 |
| TR-1395 (GCS 14) | 12,100,000,000 | 107.1 | 3489.56 | 42.4 |
| TR-1178 (GCS 14) | 89,400,000,000 | 67.7 | 136.4 | 46 |
| TR-1123 (GCS 13) | 13,400,000,000 | 124.9 | 2164.03 | 57.6 |
| TR-1161 (GCS 11) | 282,000,000,000 | 71.7 | Undetectable | 33 |
| TR-1252 (GCS 10) | 18,700,000,000 | 137.2 | 466.6 | 54.7 |
| TR-1082 (GCS 9) | 20,100,000,000 | 139 | Undetectable | 62.4 |
| TR-1330 (GCS 6T) | 8,480,000,000 | 92.7 | 1381.7 | 47.6 |
| TR-1174 (GCS 3) | 11,600,000,000 | 154.1 | Undetectable | 76.8 |
| TR-1086 (GCS 3) | 32,200,000,000 | 105 | 221.99 | 32.3 |
| TR-1219 (GCS 3) | 28,400,000,000 | 85.1 | 3834.9 | 42.6 |

TABLE 2-continued

MV/E concentration, mean size, GFAP concentration and RNA concentration

| | | | | |
|---|---|---|---|---|
| TR-1233 (GCS 3) | 31,700,000,000 | 106.6 | 13122.5 | 86.6 |
| TR-1159 (GCS 3) | 11,300,000,000 | 108.3 | 1633.1 | 16 |
| Healthy Control | | | | |
| HC-1054 (GCS 15) | 64,200,000,000 | 64.6 | Undetectable | 55.9 |
| HC-1052 (GCS 15) | 12,200,000,000 | 114 | Undetectable | 65.3 |
| HC-1015 (GCS 15) | 45,800,000,000 | 114.8 | Undetectable | 40.2 |
| HC-1019 (GCS 15) | 53,400,000,000 | 79.1 | Undetectable | 53.2 |
| HC-1058 (GCS 15) | 55,200,000,000 | 97.8 | Undetectable | 17 |

Analysis

| | Mean [MV/E] (particles/mL) | Mean MV/E size (nm) | [GFAP] (pg/mL) | [RNA] (ng/uL) |
|---|---|---|---|---|
| Altered GCS | 4.7e10±2.2e10 | 108.3 ± 7.7 | 2204.2 ± 1067.2 | 49.8 ± 5.6 |
| Normal GCS | 6.3e10±1.4e10 | 89.2 ± 6.7 | 207.8 ± 270.8 | 45.1 ± 5.9 |
| | (NS) | (NS) | ($p = 0.02$) | (NS) |

TABLE 3A

Upregulated and downregulated miRNA sequences in subjects with altered presentation GCS compared to normal presentation GCS

| Upregulated miRNA | Log2 Fold Change | p-value |
|---|---|---|
| hsa-miR-1-3p | 1.51 | $p < 0.01$ |
| hsa-miR-143-3p | 1.19 | $p < 0.01$ |
| hsa-miR-151b | 3.71 | $p = 0.09$ |
| hsa-miR-27a-3p | 0.89 | $p = 0.02$ |
| hsa-miR-29a-3p | 1.37 | $p < 0.01$ |
| hsa-miR-328-3p | 4.18 | $p = 0.09$ |
| hsa-miR-9-3p | 6.84 | $p < 0.01$ |
| hsa-miR-99a-5p | 1.32 | $p = 0.05$ |
| hsa-miR-99b-5p | 1.15 | $p = 0.06$ |
| Downregulated miRNA | | |
| hsa-miR-155-5p | -2.99 | $p = 0.03$ |
| hsa-miR-30c-5p | -1.24 | $p = 0.09$ |

TABLE 3B miRNA sequences

| miRNA | Sequence | SEQ ID NO: |
|---|---|---|
| hsa-miR-1-3p | uggaauguaaagaaguauguau | 2 |
| hsa-miR-143-3p | ugagaugaagcacuguagcuc | 3 |
| hsa-miR-151b | ucgaggagcucacagucu | 4 |
| hsa-miR-27a-3p | uucacaguggcuaaguuccgc | 5 |
| hsa-miR-29a-3p | uagcaccaucugaaaucgguua | 6 |
| hsa-miR-328-3p | cuggcccucucugcccuuccgu | 7 |
| hsa-miR-9-3p | auaaagcuagauaaccgaaagu | 8 |
| hsa-miR-99a-5p | aacccguagauccgaucuugug | 9 |
| hsa-miR-99b-5p | cacccguagaaccgaccuugcg | 10 |
| hsa-miR-155-5p | uuaaugcuaaucguguaggggu | 11 |
| hsa-miR-30c-5p | uguaaacauccuacacucucagc | 12 |

TABLE 4

Top pathways for diseases disorders or molecular and cellular functions targeted by differentially expressed plasma exosomal miRNAs, comparing TBI patients with altered consciousness (GCS < 14) and TBI patients/healthy controls with normal consciousness (GCS ≥ 14).

| Diseases and Disorders | | |
|---|---|---|
| Name | p-value range | # Molecules |
| Cancer | 4.75E-02-1.35E-12 | 10 |
| Gastrointestinal Disease | 3.84E-02-1.35E-12 | 10 |
| Organismal Injury and Abnormalities | 4.78E-02-1.35E-12 | 10 |
| Respiratory Disease | 8.49E-03-1.35E-12 | 8 |
| Reproductive System Disease | 3.43E-02-1.00E-08 | 9 |

| Molecular and Cellular Functions | | |
|---|---|---|
| Name | p-value range | # Molecules |
| Cell Death and Survival | 4.13E-02-8.72E-04 | 6 |
| Cell-to-Cell Signaling and Interaction | 1.97E-02-9.05E-04 | 4 |
| Cellular Assembly and Organization | 2.82E-02-9.05E-04 | 4 |
| Cellular Development | 4.22E-02-9.05E-04 | 9 |
| Nervous System Development and Function | 3.04E-02-9.05E-04 | 6 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method comprising:
   (a) identifying a mammal as having EVs obtained from a blood sample or plasma sample with an increased or decreased level of seven or more miRNAs as compared to a level of the seven or more miRNAs in EVs obtained from a blood sample or plasma sample of a corresponding mammal that does not have a TBI, wherein said seven or more miRNAs are selected from the group consisting of an increased level of hsa-miR-1-3p (SEQ ID NO:2), hsa-miR-143-3p (SEQ ID NO:3), hsa-miR-151b (SEQ ID NO:4), hsa-miR-27a-3p (SEQ ID NO:5), hsa-miR-29a-3p (SEQ ID NO:6), hsa-miR-328-3p (SEQ ID NO:7), hsa-miR-9-3p (SEQ ID NO:8), hsa-miR-99a-5p (SEQ ID NO:9), and hsa-miR-99b-5p (SEQ ID NO:10) and a decreased level of hsa-miR-155-5p (SEQ ID NO:11) and hsa-miR-30c-5p (SEQ ID NO:12), thereby identifying said mammal as having or being likely to have a TBI, and
   (b) treating said mammal by one or more of:
      (i) administering a medication to manage blood pressure, cerebral perfusion pressure, or intracranial pressure,
      (ii) administering an antibiotic,
      (iii) surgically removing a mass or lesion from the brain, and
      (iv) decompressing the brain via direct craniectomy and bone removal,
   wherein said treating reduces the effects of a TBI in said mammal.

2. The method of claim 1, wherein said mammal is a human.

3. The method of claim 1, wherein said EVs are from said blood sample obtained from said mammal.

4. The method of claim 1, wherein said EVs are from said plasma sample of said mammal.

5. The method of claim 1, wherein said method comprises identifying said mammal as having EVs with an increased or decreased level of nine or more miRNAs as compared to a level of the nine or more miRNAs in EVs from said corresponding mammal that does not have a TBI, wherein said nine or more miRNAs are selected from said group.

6. The method of claim 1, wherein said method comprises identifying said mammal as having EVs with an increased level of seven or more miRNAs selected from the group consisting of hsa-miR-1-3p (SEQ ID NO:2), hsa-miR-143-3p (SEQ ID NO:3), hsa-miR-151b (SEQ ID NO:4), hsa-miR-27a-3p (SEQ ID NO:5), hsa-miR-29a-3p (SEQ ID NO:6), hsa-miR-328-3p (SEQ ID NO:7), hsa-miR-9-3p (SEQ ID NO:8), hsa-miR-99a-5p (SEQ ID NO:9), and hsa-miR-99b-5p (SEQ ID NO:10), as compared to a corresponding mammal that does not have a TBI.

7. The method of claim 1, wherein said method comprises identifying said mammal as having EVs with a decreased level of one or more miRNAs selected from the group consisting of hsa-miR-155-5p (SEQ ID NO:11) and hsa-miR-30c-5p (SEQ ID NO:12), as compared to a corresponding mammal that does not have a TBI.

8. The method of claim 1, wherein said method comprises identifying said mammal as having EVs with an increased level of hsa-miR-1-3p (SEQ ID NO:2), hsa-miR-143-3p (SEQ ID NO:3), hsa-miR-151b (SEQ ID NO:4), hsa-miR-27a-3p (SEQ ID NO:5), hsa-miR-29a-3p (SEQ ID NO:6), hsa-miR-328-3p (SEQ ID NO:7), hsa-miR-9-3p (SEQ ID NO:8), hsa-miR-99a-5p (SEQ ID NO:9), and hsa-miR-99b-5p (SEQ ID NO:10), and as having a decreased level of hsa-miR-155-5p (SEQ ID NO:11) and hsa-miR-30c-5p (SEQ ID NO:12), as compared to a corresponding mammal that does not have a TBI.

* * * * *

UNITED STATES PATENT AND TRADEMARK OFFICE
CERTIFICATE OF CORRECTION

Page 1 of 1

| | |
|---|---|
| PATENT NO. | : 12,091,716 B2 |
| APPLICATION NO. | : 17/150926 |
| DATED | : September 17, 2024 |
| INVENTOR(S) | : Puffer et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 739 days.

Signed and Sealed this
Twenty-fifth Day of March, 2025

Coke Morgan Stewart
*Acting Director of the United States Patent and Trademark Office*

SEQUENCE LISTING

<160> NUMBER OF SEQ ID NOS: 12

<210> SEQ ID NO 1
<211> LENGTH: 21
<212> TYPE: DNA
<213> ORGANISM: Artificial
<220> FEATURE:
<223> OTHER INFORMATION: adapter sequence

<400> SEQUENCE: 1
agatcggaag agcacacgtc t                                    21

<210> SEQ ID NO 2
<211> LENGTH: 22
<212> TYPE: RNA
<213> ORGANISM: Homo sapiens

<400> SEQUENCE: 2
uggaauguaa agaaguaugu au                                   22

<210> SEQ ID NO 3
<211> LENGTH: 21
<212> TYPE: RNA
<213> ORGANISM: Homo sapiens

<400> SEQUENCE: 3
ugagaugaag cacuguagcu c                                    21

<210> SEQ ID NO 4
<211> LENGTH: 18
<212> TYPE: RNA
<213> ORGANISM: Homo sapiens

<400> SEQUENCE: 4
ucgaggagcu cacagucu                                        18

<210> SEQ ID NO 5
<211> LENGTH: 21
<212> TYPE: RNA
<213> ORGANISM: Homo sapiens

<400> SEQUENCE: 5
uucacagugg cuaaguuccg c                                    21

<210> SEQ ID NO 6
<211> LENGTH: 22
<212> TYPE: RNA
<213> ORGANISM: Homo sapiens

<400> SEQUENCE: 6
uagcaccauc ugaaaucggu ua                                   22

<210> SEQ ID NO 7
<211> LENGTH: 22
<212> TYPE: RNA
<213> ORGANISM: Homo sapiens

<400> SEQUENCE: 7
cuggcccucu cugcccuucc gu                                   22

<210> SEQ ID NO 8
<211> LENGTH: 22
<212> TYPE: RNA
<213> ORGANISM: Homo sapiens

<400> SEQUENCE: 8
auaaagcuag auaaccgaaa gu                                   22

<210> SEQ ID NO 9
<211> LENGTH: 22
<212> TYPE: RNA

```
<213> ORGANISM: Homo sapiens

<400> SEQUENCE: 9
aacccguaga uccgaucuug ug                                             22

<210> SEQ ID NO 10
<211> LENGTH: 22
<212> TYPE: RNA
<213> ORGANISM: Homo sapiens

<400> SEQUENCE: 10
cacccguaga accgaccuug cg                                             22

<210> SEQ ID NO 11
<211> LENGTH: 23
<212> TYPE: RNA
<213> ORGANISM: Homo sapiens

<400> SEQUENCE: 11
uuaaugcuaa ucgugauagg ggu                                            23

<210> SEQ ID NO 12
<211> LENGTH: 23
<212> TYPE: RNA
<213> ORGANISM: Homo sapiens

<400> SEQUENCE: 12
uguaaacauc cuacacucuc agc                                            23
```